United States Patent
Soranzo et al.

(10) Patent No.: US 8,349,355 B2
(45) Date of Patent: Jan. 8, 2013

(54) FORMULATIONS OF LIPOIC ACID AND HYALUROINC ACID AND/OR THE DERIVATIVES THEREOF IN THE PHARMACEUTICAL AND COSMETIC FIELDS

(75) Inventors: Carlo Soranzo, Padua (IT); Doriana Senigaglia, Padua (IT); Davide Bellini, Albignasego (IT)

(73) Assignee: Anika Therapeutics S.R.L., Abano Terme (PD) (IT)

(*) Notice: Subject to any disclaimer, the term of this patent is extended or adjusted under 35 U.S.C. 154(b) by 812 days.

(21) Appl. No.: 11/921,247

(22) PCT Filed: May 24, 2006

(86) PCT No.: PCT/EP2006/004914
§ 371 (c)(1),
(2), (4) Date: Jun. 23, 2009

(87) PCT Pub. No.: WO2006/128618
PCT Pub. Date: Dec. 7, 2006

(65) Prior Publication Data
US 2009/0304758 A1    Dec. 10, 2009

(30) Foreign Application Priority Data
Jun. 1, 2005 (IT) .................. PD2005A0168

(51) Int. Cl.
*A61L 15/16* (2006.01)
*A61L 15/00* (2006.01)
*A61F 13/00* (2006.01)
*A61K 9/70* (2006.01)
*A61K 31/715* (2006.01)
*A01N 43/04* (2006.01)

(52) U.S. Cl. ........ 424/444; 424/443; 424/445; 424/447; 514/54

(58) Field of Classification Search .................. 424/444, 424/443, 445, 447; 514/54
See application file for complete search history.

(56) References Cited

U.S. PATENT DOCUMENTS

| 5,084,481 A | 1/1992 | Ulrich et al. |
| 5,520,916 A * | 5/1996 | Dorigatti et al. ............... 424/402 |
| 5,925,366 A | 7/1999 | Wolf et al. |
| 5,965,618 A * | 10/1999 | Perricone ....................... 514/558 |
| 2004/0105873 A1 | 6/2004 | Gupta |
| 2004/0191330 A1 | 9/2004 | Keefe et al. |
| 2004/0265268 A1 | 12/2004 | Jain |

FOREIGN PATENT DOCUMENTS

| DE | 102 58 239 | 6/2004 |
| EP | 0 582 330 | 2/1994 |
| EP | 0 855 396 | 7/1998 |
| FR | 2 820 635 | 8/2002 |
| JP | 2001-212170 | 8/2001 |
| WO | 97/10808 | 3/1997 |
| WO | 01/00190 | 1/2001 |

OTHER PUBLICATIONS

Beitner, H. "Randomized, placebo-controlled, double blind study on the clinical efficacy of a cream containing 5% α-lipoic acid related to photoageing facial skin" *British Journal of Dermatology*, vol. 149, (2003), pp. 841-849.
English translation of abstracts of Japan of JP 2001-212170 dated Aug. 7, 2001.

* cited by examiner

*Primary Examiner* — Gina C Justice
*Assistant Examiner* — Michael B Pallay
(74) *Attorney, Agent, or Firm* — Ladas & Parry LLP

(57) ABSTRACT

The present invention relates to novel formulations comprising lipoic acid and hyaluronic acid and/or the derivatives thereof for use in the repair of chronic ulcers, the regeneration of damaged skin, the prevention of skin aging and, when administered by the systemic route, to treat peripheral neuropathies and intoxications by chemical and/or biological agents.

9 Claims, No Drawings

FORMULATIONS OF LIPOIC ACID AND HYALUROINC ACID AND/OR THE DERIVATIVES THEREOF IN THE PHARMACEUTICAL AND COSMETIC FIELDS

SUBJECT OF THE INVENTION

The present invention relates to novel formulations comprising lipoic acid and hyaluronic acid and/or the derivatives thereof for use in the repair of chronic ulcers, the regeneration of damaged skin, the prevention of skin aging and, when administered by the systemic route, to treat peripheral neuropathies and intoxications by chemical and/or biological agents.

FIELD OF THE INVENTION

Lipoic acid, also known as α-lipoic acid or thioctic acid, is a molecule physiologically produced by human body, in which it plays a role as co-factor in important enzymatic reactions in various metabolic processes, including Kreb's cycle. Due to its chemical structure, lipoic acid is prone to oxidation-reduction reactions, giving its reduced form of dihydrolipoic acid. It is also able to act as a carrier for electrons or acetyl groups or other acyls. Lipoic acid has some special features that make it not only extraordinarily effective as an antioxidant but also absolutely indispensable to human body in fighting the damage associated with free radicals formation. These features are:

high absorbability: being a relatively small molecule, it is readily absorbed and transported across the cell membranes;

versatility: being soluble in both water and lipids, it remains active both in aqueous cell compartments (cytoplasm, extracellular fluids) and in lipid compartments (cell membranes);

oxidating potential: oxidating activity is exercised both by the reduced (dihydrolipoic acid) and oxidized forms;

broad spectrum activity: it is active against numerous radicalic species, such as superoxides, hydroperoxides, peroxyhydroxy- and peroxynitric-type radicals. Both lipoic acid and dihydrolipoic acid are also chelators of iron, copper and other transition metals responsible for oxidative stress conditions (Scott B et al., *Free Rad Res,* 1994, 20:119-133).

Due to these properties (see also: Reed L J, *Adv Enzymol,* 1957, 18:319) lipoic acid acts in numerous compartments of the human organism, enhancing, for example, the regeneration of other antioxidants, such as vitamin C and indirectly vitamin E, improving the transport of glucose within cells while increasing the efficiency of insulin (Jacob S et al., *Diabetes,* 1996, 45:1024-1029), protecting nerves from damage in various ways (protecting them from free radicals, increasing their conduction velocity and the production of neuropeptide Y with consequent antalgic effect), stimulating the reactivity of liver cells damaged by fungal toxins, markedly increasing the wound healing processes in skin damaged by conditions involving free radicals (autoimmune diseases, irritative, atopic, contact and allergic dermatitis, inflammatory disorders, wounds, ulcers, aging and/or photoaging).

It has been demonstrated that lipoic acid administered by either the oral or parenteral route is effective in protecting the skin from inflammation (Fuchs J et al., *Skin Pharmacol,* 1994:278-284) and improving wound healing (Di Mezza F., *Arch Ital Sci Farmacol,* 1961, 11:339-340). Patent literature also contains descriptions of methods for treating damaged skin by using lipoic acid and the derivatives thereof in association with other active ingredients (EP 863744) formulated in carriers commonly used in dermatology and/or cosmetics; the scientific literature contains reports of the use of a lipoic-acid-based cream which decidedly improves the appearance of skin damaged by photoaging (Beitner H., Br J Dermatol, 2003, 149:841-849).

The present invention relates to novel formulations of lipoic acid associated with a polysaccharide which remarkably improves its performance in terms of distribution homogeneity and, thanks to its peculiar features, acts synergically with lipoic acid, enhancing its antioxidant, anti-inflammatory, free-radical-scavenging and wound healing effects. Thus, the limitations of the current state of the art, where lipoic acid is simply vehicled in pharmaceutical/cosmetic carriers, are overcome. According to the invention, the polysaccharide associated with lipoic acid is hyaluronic acid (HA), known for its ability to act as a delivery system for the release of pharmacologically and/or biologically active substances to be administered by the topical route (EP 197718); hyaluronic acid also exerts anti-inflammatory action by inhibiting the activity of inflammatory cytokines such as interleukin 1 (IL-1) and Tumour Necrosis factor (TNF).

HA is a heteropolysaccharide composed of alternating residues of D-glucuronic acid and N-acetyl-D-glucosamine. It is a linear-chained polymer with a molecular weight that varies between 50,000 and $13 \times 10^6$ Da, according to the source from which it is obtained and the methods used to prepare it. HA is ubiquitous in nature (for example in the pericellular gels, the fundamental substance of connective tissue in vertebrate organisms, in the synovial fluid of joints, the vitreous humor, the umbilical cord) and exercises numerous important functions in the biological organism. It acts as a mechanical support for the cells of many tissues, such as the skin, the tendons, the muscles and the cartilage, and by means of its membrane receptor CD44, it modulates many processes involved in cell physiology and biology, such as cell proliferation, migration and differentiation, and angiogenesis. It has also been demonstrated that HA plays a fundamental role in the tissue repair process, both from a structural point of view (in organising the extracellular matrix and regulating its hydration) and as stimulator of a vast series of processes in which it intervenes either directly or indirectly (clot formation, phagocyte activity, fibroblast proliferation, neovascularisation, re-epithelialisation, etc.) (Weigel P. et al., *J Theoretical Biol,* 1986:219-234; Abatangelo G. et al., *J Surg Res,* 1983, 35:410-416; Goa K. et al., *Drugs,* 1994, 47:536-566). Hyaluronic acid has been chemically modified in order to improve its mechanical features, without however altering its biological properties of biocompatibility and biodegradability, giving:

HA salified with organic and/or inorganic bases (EP 138572 B1);

HYAFF®: HA esters with aliphatic, araliphatic, cycloaliphatic, aromatic, cyclic and heterocyclic alcohols, with an esterification degree that may vary according to the type and length of the alcohol used, preferably between 0.1 and 100%, while the remaining percentage of unesterified HA may be salified with organic and/or inorganic bases (EP 216453 B1);

HYADD™: amides of HA with aliphatic, araliphatic, cycloaliphatic, aromatic, cyclic and heterocyclic amines, with an amidation degree of between 0.1 and 50%, while the remaining percentage of HA that has not been amidated may be salified with organic and/or inorganic bases (EP 1095064 B1);

O-sulphated derivatives of HA up to the $4^{th}$ degree of sulphation (EP 702699 B1);

ACP®: inner esters of HA with an esterification degree not exceeding 20%, preferably between 0.05 and 10% of esterification, while the remaining percentage of HA that has not been esterified may be salified with organic and/or inorganic bases (EP 341745 B1);

deacetylated products of HA: derive from deacetylation of the N-acetyl-glucosamine fraction with a preferred a deacetylation degree between 0.1 and 30%, while all the carboxy groups of HA may be salified with organic and/or inorganic bases (EP 1313772 B1);

HYOXX™: percarboxylated derivatives of HA obtained by oxidating the primary hydroxyl of the N-acetyl-glucosamine fraction with a percarboxylation degree of between 0.1 and 100% and preferably between 25 and 75%. All the carboxy groups of HA can be salified with organic and/or inorganic bases (EP 1339753).

Also known is the use of HA derivatives in the formation of fibres (EP 618817) which, when worked into a non-woven fabric, constitute a three-dimensional matrix that can be used in the field of dermatology.

The hyaluronic acid used in the present invention may be obtained from any source, for example by extraction from rooster combs (EP 138572), by fermentation (EP 716688), or by technological means, and may have a molecular weight ranging between 400 and $3\times10^6$ Da.

DETAILED DESCRIPTION OF THE INVENTION

The present invention relates to formulations of lipoic acid associated with hyaluronic acid and/or the derivatives thereof to be used substantially for the topical treatment of all skin conditions characterised by oxidative stress and the massive presence of free radicals, such as autoimmune diseases, or irritative, atopic, contact or allergic dermatitis, inflammatory states, wounds, or ulcers. The formulations of the present invention are also suitable for the dermocosmetic treatment of the signs of aging and photoaging of the skin. In the present invention, lipoic acid used at concentrations ranging between 0.5 and 15%, and preferably between 1 and 10%, has been successfully associated with both hyaluronic acid as such and with the derivatives thereof obtained by chemical modification by salification, inner esterification (ACP®), percarboxylation (HYOXX™), O-sulphation, amidation (HYADD™), deacetylation and esterification with alcohols of the aliphatic, araliphatic, cycloaliphatic, aromatic, cyclic and heterocyclic series (HYAFF®).

The derivatives obtained as described herein maintain the biological properties of biocompatibility and biodegradability of the starting molecule, but they give a better mechanical performance, with better bioadhesiveness, a controlled release of the lipoic acid and a residence time of the final association of HA/lipoic acid that significantly enhances all the chemical-physical, biological and pharmacological properties of both hyaluronic acid and lipoic acid.

Thanks to their special features, the formulations described herein can also be used for the systemic and/or locoregional administration, for example in treatment of intoxication by chemical and/or biological agents and in peripheral neuropathies. Of the various conditions that can benefit from topical administration of the formulations described herein, particularly important are venous ulcers. Venous ulcers of the lower limbs have considerable social impact because of their incidence in the population (about 1%) and slow rate of healing. Generally, repair of chronic ulcers is seriously hampered by the disregulating effect of chronic inflammation on both the cytokine cascade and the physiological repair processes. In particular, venous ulcers are characterised by overexpression of metalloprotease (MMP) which, together with the disappearance of their physiological tissue inhibitors, determine excessive proteolysis of the extracellular matrix (ECM). Such pathological proteolysis is determined by the presence, in the tissues surrounding the ulcer, of a considerable quantity of iron which induces the formation of free radicals and the recruitment of macrophages which undergo oxidative stress as a result of excessive phagocytosis of the metal. The abundance of iron activates MMP expression as described above, and MMP activity is further amplified by feedback established by the ECM degradation products themselves. The problem of healing venous ulcers is therefore solved by the formulations that are the subject of the present invention, constituted by lipoic acid and hyaluronic acid and/or the derivatives thereof. Lipoic acid, being an antioxidant and iron chelator, takes the free radicals, especially iron, from the tissues surrounding the ulcer, hindering the action of MMP and thus favouring the formation of ECM. Lipoic acid is aided in this by the presence of hyaluronic acid and/or the derivatives thereof. Of the numerous derivatives, particularly useful for this type of application is the benzyl ester of hyaluronic acid (HYAFF®-11) in which the percentage of esterification ranges from 0.1 to 100%, preferably between 50 and 100% and more preferably still between 75 and 100%. Worked in the form of a non-woven fabric, it forms a soft pad that can be adapted to fit the shape and size of the ulcer, and is also bioadhesive. Its hyaluronic acid content is active at various levels:

It creates a moist environment that favours wound healing

It contributes to the formation and organisation of the extracellular matrix

It combats tissue inflammation by opposing the activity of IL-1 and other inflammatory cytokines It favours fibroblast proliferation, neovascularisation, re-epithelialisation, and therefore the repair of damaged tissue It ensures an even distribution of lipoic acid The synergic action of the formulations of the present invention causes faster, more effective healing of the ulcer than can be achieved with the dressings available to date. New therapeutic possibilities are therefore opened up that go beyond the current state of the art.

Similar results are achieved by using, according to the type of lesion to be treated, hyaluronic acid and/or the derivatives thereof in the form of a gel, cream, ointment, lotion, suspension for intradermal/subcutaneous use (including fillers) for the treatment of skin disorders such as dermatitis of various kinds and autoimmune diseases, for the prevention and dermocosmetic cure of the signs of aging and photoaging and for all skin manifestations characterised by a non-physiological presence of free radicals and alterations in the oxidation-reduction balance. In such situations the antioxidant effect and free-radical-scavenger effect of lipoic acid are enhanced and amplified by the presence of HA and/or the derivatives thereof. Moreover, hyaluronic acid ensures an even distribution of lipoic acid within the formulation thus guaranteeing its constant and continuous release once administered.

Therefore, the invention also relates to formulations of lipoic acid associated with hyaluronic acid and/or the derivatives thereof for the systemic administration such as oral, rectal, locoregional, injective (intradermal, subcutaneous, intramuscular, intravenous, intraperitoneal) routes, for use in the treatment of other disorders that benefit from free radical scavenging, such as intoxication by chemical and/or biological agents: besides the effects described previously, HA, rapidly captured by the liver cells, enables the lipoic acid to act specifically on the liver cells by interacting with its membrane receptor CD44, thus stimulating their regeneration;

peripheral neuropathies: HA contributes significantly to a profile of smooth, constant and continuous release.

For purely descriptive purposes, and without being limited by the same, The present invention is disclosed in more detail in the following examples.

Example 1

Preparation of a Formulation Constituted by a Non-Woven Fabric of HYAFF® 11-p75 Impregnated with Lipoic Acid A non-woven fabric of HYAFF® 11-p75 measuring 10×10 cm is soaked with a 5% solution of lipoic acid in absolute ethanol. The treatment involves leaving the non-woven fabric in the ethanol solution of lipoic acid for 3 minutes. At the end of this time, the excess liquid is discarded and the non-woven fabric is dried by eliminating the residue solvent by vacuum extraction on a hotplate heated to 30° C. The product is then analysed to determine the quantity of lipoic acid that has been absorbed by the non-woven fabric, which should be between 100 and 200 mg for each piece measuring 10×10 cm.

Example 2

Preparation of a Formulation Constituted by a Percarboxylated Derivative of Hyaluronic Acid (HYOXX™) and Lipoic Acid The percarboxylated derivative is solubilised in DMF (dimethylformamide) at a concentration of 80-120 mg/ml, and coagulated in a solution constituted by 2% lipoic acid in absolute ethanol. This treatment enables the lipoic acid to be absorbed by the percarboxylated derivative. The product, in the form of a film, is dried in a vacuum on a hotplate heated to 30° C., and analysed to determine the quantity of lipoic acid it contains, which should be between 100 and 200 mg for each piece measuring 10×10 cm.

Example 3

Preparation of a Formulation containing Sulphated Hyaluronic Acid with a Degree of Sulphation of 3 and Lipoic Acid 5 grams of sulphated hyaluronic acid with a degree of sulphation of 3 (7.05 millimole) and a mean molecular weight of 200 Kda is solubilised in 50 ml of water. The solution is vigorously stirred with a magnetic stirrer while slowly adding a solution of 1% lipoic acid in ethanol, prepared by dissolving 500 mg of lipoic acid in 50 ml of 96% ethanol.

The resulting emulsion is freeze-dried.

The product thus obtained is analysed to determine the quantity of lipoic acid contained in the freeze-dried product, which should be between 80 and 100 mg of lipoic acid per gram of sulphated derivative.

Example 4

Preparation of a Formulation containing an Amide Derivative of Hyaluronic Acid with Dodecyl Amine and Lipoic Acid 2 grams of dodecyl amide of hyaluronic acid (HYADD™-3) at 5% (4.88 millimole) with a mean molecular weight of 200 Kda is solubilised in 100 ml of water. The solution is vigorously stirred with a magnetic stirrer while slowly adding a solution of 20% lipoic acid in 96% ethanol, prepared by dissolving 200 mg of lipoic acid in 1 ml of 96% ethanol. The resulting emulsion is transferred in a 2-ml glass syringe and steam-sterilised. A topical dressing in the form of a sterile gel comprising an amide derivative containing 10% lipoic acid is thus obtained. The product is analysed to determine the quantity of lipoic acid contained in the gel, which should be between 80 and 100 mg of lipoic acid per gram of amide derivative of hyaluronic acid.

Example 5

Preparation of a Formulation containing an Amide Derivative of Hyaluronic Acid with Hexadecyl Amine and Lipoic Acid 2 grams of hexadecyl amide of hyaluronic acid (HYADD™-4) at 3% (4.90 millimole) with a mean molecular weight of 500 Kda is solubilised in 100 ml of water. The solution is vigorously stirred with a magnetic stirrer while slowly adding a solution of 10% lipoic acid in 96% ethanol, prepared by dissolving 100 mg of lipoic acid in 1 ml of 96% ethanol. The resulting emulsion is transferred into a 2-ml glass syringe and steam-sterilised. A topical dressing in the form of a sterile gel comprising an amide derivative of hyaluronic acid containing 5% lipoic acid is thus obtained. The product is analysed to determine the quantity of lipoic acid container in the gel, which should be between 40 and 50 mg of lipoic acid per gram of amide derivative of hyaluronic acid.

Example 6

Preparation of a Formulation containing an Auto-Cross-Linked Derivative of Hyaluronic Acid (ACP®) and Lipoic Acid 1 gram of hyaluronic acid cross-linked to a degree of 10% (2.52 millimole) with a mean molecular weight of 200 Kda is solubilised in 100 ml of water. The solution is vigorously stirred with a magnetic stirrer while slowly adding a solution of 10% lipoic acid in 96% ethanol, prepared by dissolving 100 milligrams of lipoic acid in 1 ml of 96% ethanol. The resulting emulsion is transferred to a 2-mi glass syringe and steam-sterilised. A topical dressing in the form of a sterile gel comprising an auto-cross-linked derivative of hyaluronic acid containing 10% lipoic acid is thus obtained.

The product is analysed to determine the quantity of lipoic acid contained in the gel, which should be between 80 and 100 mg of lipoic acid per gram of cross-linked derivative of hyaluronic acid.

Example 7

Preparation of a Formulation containing a Mixture of Hyaluronic Acid Sodium Salt and Lipoic Acid A prefilled syringe of 2 ml contains:

| | |
|---|---|
| Hyaluronic acid sodium salt (PM 500 Kda) | 15 mg |
| lipoic acid | 5 mg |
| sodium chloride | 17 mg |
| sodium phosphate monobasic dihydrate | 0.1 mg |

-continued

| | |
|---|---|
| sodium phosphate dibasic dodecahydrate | 1.2 mg |
| water for injection | 2 ml |

The resulting suspension is suitable for injection and packed in prefilled syringes and steam-sterilised.

Example 8

Preparation of a Formulation Containing a Mixture Comprising Auto-Cross-Linked Hyaluronic Acid and Lipoic Acid A prefilled syringe of 2 ml contains:

| | |
|---|---|
| auto-cross-linked hyaluronic acid (ACP ®) | 15 mg |
| lipoic acid | 5 mg |
| sodium chloride | 17 mg |
| sodium phosphate monobasic dihydrate | 0.1 mg |
| sodium phosphate dibasic dodecahydrate | 1.2 mg |
| water for injection | 2 ml |

The resulting suspension is suitable for injection and packed in prefilled syringes and steam-sterilised.

The invention claimed is:

1. A topical composition comprising lipoic acid and the benzyl ester of hyaluronic acid with an esterification degree of 75%.

2. The composition according to claim 1, wherein the percentage of lipoic acid varies between 0.5 and 15%.

3. The composition according to claim 2, wherein the percentage of lipoic acid varies between 1 and 10%.

4. The composition according to claim 1, in the form of non-woven fabric, cream, gel, lotion, or ointment.

5. The composition according to claim 4 in the form of a non-woven fabric.

6. A method of treating skin lesions which comprises topically applying thereto a combination of lipoic acid and of the benzyl ester of hyaluronic acid with an esterification degree of from 75%.

7. The method according to claim 6, wherein the skin lesions are chronic ulcers, wounds, skin inflammation, autoimmune disorders, irritative, atopic or contact dermatitis, signs of aging or photoaging.

8. The method according to claim 7 which comprises topical treatment of chronic ulcers.

9. A process for preparing the composition according to claim 5 comprising the steps of:
   preparing an ethanol solution of lipoic acid,
   soaking in said solution a non-woven fabric made of the benzyl ester of hyaluronic acid with an esterification degree of 75%, and
   drying the non-woven fabric by vacuum extraction on a hotplate.

* * * * *